US012796947B2

(12) United States Patent
Jeon et al.

(10) Patent No.: US 12,796,947 B2
(45) Date of Patent: Nov. 17, 2026

(54) SMART RING FOR MEASURING BIOMETRIC SIGNAL

(71) Applicant: SKY LABS INC., Seongnam (KR)

(72) Inventors: Sang Yeun Jeon, Yongin-si (KR); Jeong Yeol Kim, Siheung-si-Gyeonggi-do (KR); Chang Woo Choi, Uiwang-si (KR); Byung Hwan Lee, Yongin-si (KR)

(73) Assignee: Sky Labs Inc., Seongnam-si (KR)

( * ) Notice: Subject to any disclaimer, the term of this patent is extended or adjusted under 35 U.S.C. 154(b) by 212 days.

(21) Appl. No.: 18/691,847

(22) PCT Filed: Sep. 14, 2022

(86) PCT No.: PCT/KR2022/013733
§ 371 (c)(1),
(2) Date: Mar. 13, 2024

(87) PCT Pub. No.: WO2023/043194
PCT Pub. Date: Mar. 23, 2023

(65) Prior Publication Data

US 2025/0017479 A1 Jan. 16, 2025

(30) Foreign Application Priority Data

Sep. 15, 2021 (KR) ........................ 10-2021-0123169

(51) Int. Cl.
*A61B 5/024* (2006.01)
*A61B 5/00* (2006.01)
*A61B 5/01* (2006.01)

(52) U.S. Cl.
CPC ............ *A61B 5/02427* (2013.01); *A61B 5/01* (2013.01); *A61B 5/6826* (2013.01); *A61B 5/6885* (2013.01)

(58) Field of Classification Search
CPC ..... A61B 5/02427; A61B 5/01; A61B 5/6826; A61B 5/6885; A61B 5/02416;
(Continued)

(56) References Cited

U.S. PATENT DOCUMENTS 8,131,347 B2 3/2012 Cho et al.
10,085,652 B2 10/2018 Baek et al.
(Continued)

FOREIGN PATENT DOCUMENTS

CN 101347328 A 1/2009
CN 108618763 A 10/2018
(Continued)

OTHER PUBLICATIONS

Laser Focus Word Japan, "Optical heart rate measurement expands healthcare applications," (May 26, 2016) (Cited in Japanese Patent Office, Decision on Refusal in Japanese Patent Application No. 2024-516832 (Jan. 24, 2025) as being obtained from <<http://web.archive.org/web/20250325075537/https://ex-press.jp/lfwj/lfwj-news/lfwj-biz-market/13348/>>).
(Continued)

*Primary Examiner* — Joseph M Dietrich
(74) *Attorney, Agent, or Firm* — Leydig, Voit & Mayer, Ltd.

(57) ABSTRACT

A smart ring for sensing a biometric signal is provided. The smart ring for sensing a biometric signal by coming in contact with the skin includes at least one light-emitting circuit including first to third light sources that respectively generate light of first to third wavelengths incident on the inside of the skin at non-overlapping first to third points in time, a switch that controls each of the at least one light-emitting circuit, first to third driving circuits that respectively control the first to third light sources of each light-emitting circuit, and a sensing circuit configured to obtain
(Continued)

reflected light that is output from the at least one light-emitting circuit and reflected from the inside of the skin.

12 Claims, 8 Drawing Sheets

(58) Field of Classification Search
CPC . A61B 5/02438; A61B 5/024; A61B 5/02433; A61B 5/14552
See application file for complete search history.

(56) References Cited

U.S. PATENT DOCUMENTS

| | | | |
|---|---|---|---|
| 10,918,289 | B1 | 2/2021 | Wasson et al. |
| 2006/0211932 | A1 | 9/2006 | Al-Ali et al. |
| 2007/0060807 | A1 | 3/2007 | Oishi |
| 2012/0046530 | A1 | 2/2012 | Al-Ali et al. |
| 2015/0220109 | A1 | 8/2015 | von Badinski et al. |
| 2015/0340351 | A1 | 11/2015 | Rossi et al. |
| 2016/0166161 | A1 | 6/2016 | Yang et al. |
| 2017/0079534 | A1* | 3/2017 | Tchertkov .............. A61B 5/681 |
| 2020/0000345 | A1 | 1/2020 | Conner |
| 2020/0085327 | A1 | 3/2020 | Zhou et al. |
| 2020/0253562 | A1 | 8/2020 | Newberry et al. |
| 2021/0030372 | A1 | 2/2021 | Lizio et al. |
| 2021/0037932 | A1* | 2/2021 | Min ..................... A61B 5/0006 |
| 2021/0169345 | A1 | 6/2021 | Wasson et al. |
| 2021/0244302 | A1 | 8/2021 | Lizio et al. |
| 2022/0256984 | A1 | 8/2022 | Min et al. |
| 2025/0017479 | A1 | 1/2025 | Jeon et al. |

FOREIGN PATENT DOCUMENTS

| | | | |
|---|---|---|---|
| CN | 109152925 | A | 1/2019 |
| JP | 2008-194186 | A | 8/2009 |
| JP | 2017-131445 | A | 8/2017 |
| JP | 2019-513035 | A | 5/2019 |
| JP | 2021-519621 | A | 8/2021 |
| JP | 7737756 | B2 | 9/2025 |
| KR | 10-2007-0024432 | A | 3/2007 |
| KR | 10-2017-0091346 | A | 8/2017 |
| KR | 10-2018-0056714 | A | 5/2018 |
| KR | 10-2019-0105421 | A | 9/2019 |

OTHER PUBLICATIONS

Yan et al., "A Multiplexed Electronic Architecture for Optoelectronic Patch Sensor to Effectively Monitor Heart Rate and Oxygen Saturation," Progress in Biomedical Optics and Imaging, SPIE-International Society for Optical Engineering, Bellingham, WA, US, 10501: 1050115, XP060100004 (Feb. 20, 2018).
European Patent Office, Extended European Search Report in European Patent Application No. 22870278.3 (Jan. 31, 2025).
Japanese Patent Office, Decision on Refusal in Japanese Patent Application No. 2024-516832 (Jan. 24, 2025).
International Search Report and Written Opinion issued in PCT/KR2022/013733 mailed on Dec. 12, 2022.
Non-Final Office Action issued in KR 10-2021-0123169, 8 pages, dated Apr. 27, 2023.
Notice of Allowance issued in KR 10-2021-0123169, 6 pages, dated Oct. 19, 2023.
China National Intellectual Property Administration, Office Action in Chinese Application No. 202280062720.3 (issued Aug. 31, 2026).
European Patent Office, Office Action in European Patent Application No. 22870278.3-1113 (Apr. 15, 2026).
Japan Patent Office, Office Action in Japanese Patent Application No. 2025-139907 (Aug. 21, 2026).

* cited by examiner

SMART RING FOR MEASURING BIOMETRIC SIGNAL

TECHNICAL FIELD

The present disclosure relates to a smart ring, and more specifically, to a smart ring capable of measuring biometric signals such as electrocardiogram, blood pressure, and the like.

BACKGROUND ART

The wearable healthcare market is expanding due to the convergence of information and communication technology and medical services. Wearable products include various sensors to collect a user's heart rate, amount of exercise, and location information, and transmit these to a mobile device connected to the wearable products.

As an example, a wearable product may include a photoplethysmography (PPG) sensor. A PPG sensor can measure changes in the blood flow by optically detecting light reflected or transmitted from tissues and blood. The heart rate, blood pressure, respiration, and blood oxygen saturation can be predicted based on information measured by the PPG sensor.

A PPG sensor generally consists of two light-emitting diodes (LEDs) and one optical sensor. Specifically, light from an LED enters the skin and is partially absorbed and scattered within the tissue, and the transmitted and reflected light is sensed by an optical sensor. Since the amount of light absorbed within the tissue varies greatly with the blood flow, the blood flow can be measured based on the amount of light measured by the optical sensor.

Wearable products are required to be easy to carry and worn on a user's body for a long period of time, and thus, there may be limitations in a product size and area in contact with the skin. Therefore, there are limitations on the size or number of sensors that can be installed in wearable products.

DISCLOSURE

Technical Problem

The objective to be solved by the present disclosure is to provide a smart ring that is capable of sensing a biometric signal and includes light sources arranged in a matrix form.

Technical Solution

In order to achieve the above objective, a smart ring capable of sensing a biometric signal by coming in contact with the skin, according to an aspect of the present disclosure, includes at least one light-emitting circuit including first to third light sources that respectively generate light of first to third wavelengths incident on the inside of the skin at non-overlapping first to third points in time, a switch that controls each of the at least one light-emitting circuit, first to third driving circuits that respectively control the first to third light sources of each light-emitting circuit, and a sensing circuit configured to obtain reflected light that is output from the at least one light-emitting circuit and reflected from the inside of the skin.

As an example, the at least one light-emitting circuit may include first and second light-emitting circuits provided on an inner side surface where the smart ring and the skin contact each other, and the first and second light-emitting circuits may be arranged adjacent to each other.

As an example, a light source that generates light of the first wavelength in the first light-emitting circuit and a light source that generates light of the first wavelength in the second light-emitting circuit may be arranged adjacent to each other.

As an example, the at least one light-emitting circuit may include first and second light-emitting circuits provided on an inner side surface where the smart ring and the skin contact each other, and the first and second light-emitting circuits may be arranged such that a distance between the first and second light-emitting circuits is equal to a diameter of the smart ring.

As an example, the at least one light-emitting circuit may include first to nth light-emitting circuits (where n is a natural number equal to or greater than 3) provided on an inner side surface where the smart ring and the skin contact each other, and the first to nth light-emitting circuits may be uniformly disposed on the inner side surface.

As an example, the inner side surface of the smart ring, which is in contact with the skin, may be formed as a polygonal pillar, each light-emitting circuit may be provided on each side of the polygonal pillar, and a first light-emitting circuit group of the at least one light-emitting circuit may operate in a first operation mode, and a second light-emitting circuit group of the at least one light-emitting circuit may operate in a second operation mode.

As an example, the first light-emitting circuit group may include first and second light-emitting circuits respectively disposed on adjacent sides of the polygonal pillar, and the second light-emitting circuit group may include third and fourth light-emitting circuits respectively disposed on opposite sides of the polygonal pillar which face each other.

As an example, first to third light sources of the first to fourth light-emitting circuits may be sequentially arranged in a first direction corresponding to a height direction of the smart ring.

As an example, the first to third driving circuits may sequentially drive first to third light sources of each of the first and second light-emitting circuits in the first operation mode, and sequentially drive first to third light sources of each of the third and fourth light-emitting circuits in the second operation mode.

As an example, the first to third wavelengths may include a red region, a green region, and an infrared region, respectively.

As an example, the first to third driving circuits may control each cycle of driving each of the first to third light sources of each light-emitting circuit according to at least one of the biometric signal and a control signal generated based on the biometric signal.

As an example, the first to third driving circuits may control cycles for driving the first to third light sources such that a driving cycle of the first to third light sources of each of the first and second light-emitting circuits is different from a driving cycle of the first to third light sources of each of the third and fourth light-emitting circuits.

As an example, the smart ring may further include a temperature sensor that measures a temperature of the skin, wherein the first to third driving circuits control each cycle for driving each of the first to third light sources of each light-emitting circuit based on the temperature measured by the temperature sensor.

Advantageous Effects

A smart ring that measures a biometric signal, according to the present disclosure, includes light sources arranged in a matrix form, and thus, the number of light sources mounted on the smart ring which has a limited area may be increased, and accordingly, the intensity of light may increase, thereby increasing the accuracy of measured biometric signals.

In addition, according to the smart ring that measures a biometric signal, according to the present disclosure, the smart ring may be used in various sensing modes by selectively operating some light-emitting circuits among a plurality of light-emitting circuits.

BEST MODE

Mode for Invention

Figure 1:
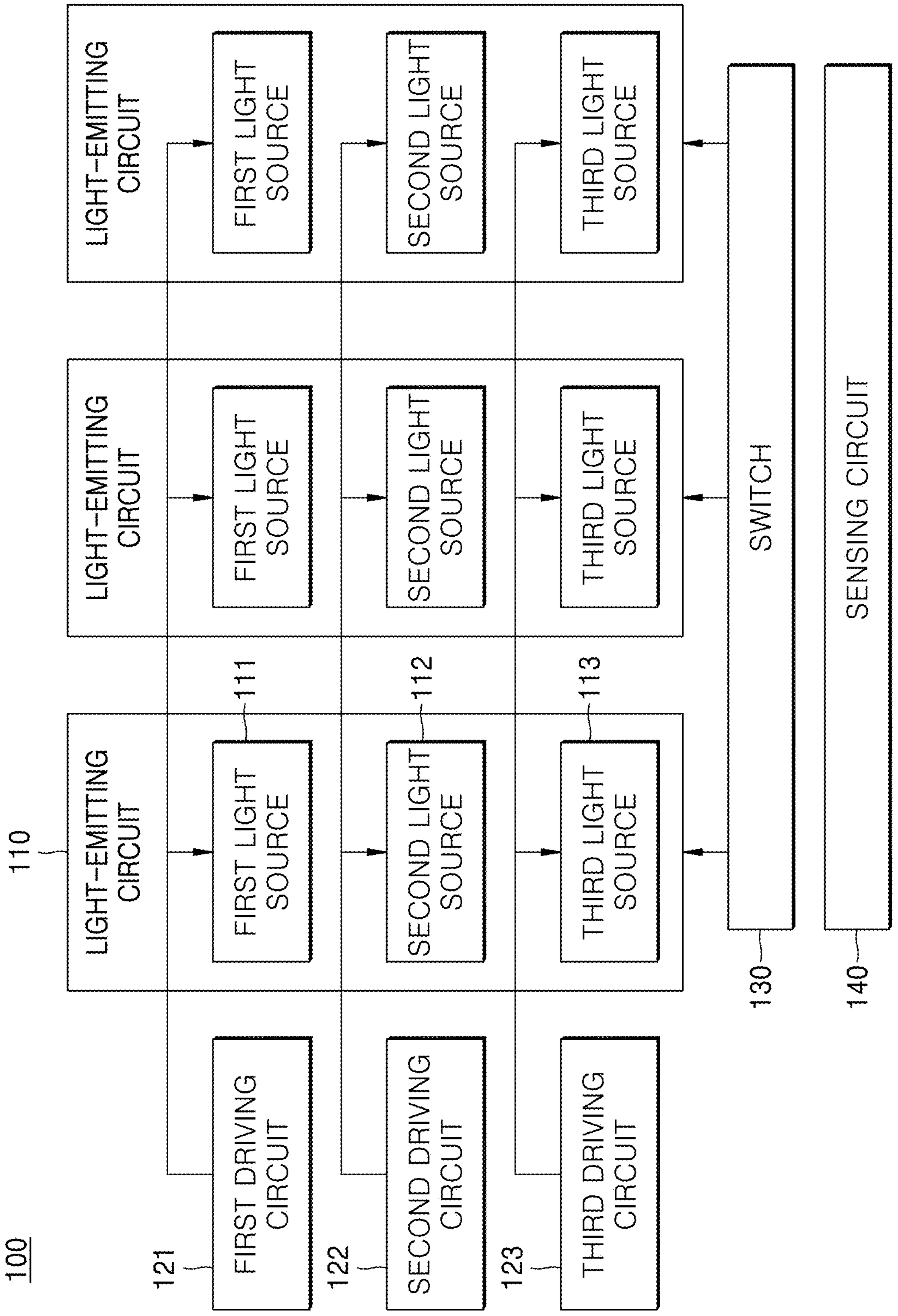
FIG. 1 is a block diagram of a smart ring according to an example embodiment of the present disclosure.

Hereinafter, the present disclosure will now be described more fully with reference to the accompanying drawings, in which exemplary embodiments of the present disclosure are shown such that one of ordinary skill in the art may easily work the present disclosure. The present disclosure may, however, be embodied in many different forms and should not be construed as limited to the embodiments set forth herein. Also, elements not related to description are omitted in the drawings for clear description of the present disclosure, and like reference numerals in the drawings denote like elements throughout the specification.

Throughout the specification, it will also be understood that when a component "includes" an element, unless there is another opposite description thereto, it should be understood that the component does not exclude another element but may further include another element. In addition, terms such as " . . . unit", " . . . er/or", " . . . module", or the like refer to units that perform at least one function or operation, and the units may be implemented as hardware or software or as a combination of hardware and software.

Throughout the specification, it will also be understood that when an element is referred to as being "connected to" another element, it can be directly connected to the other element, or it can be electrically connected to the other element and intervening elements may be present. In addition, throughout the specification, it will also be understood that when a component "includes" an element, unless there is another opposite description thereto, it should be understood that the component does not exclude another element but may further include another element, and it is to be understood that the term is not intended to preclude the possibility that one or more other features, numbers, steps, actions, components, parts, or combinations thereof may be added.

In the present specification, a smart ring may refer to a wearable device worn on the finger of a user. The smart ring may contact the finger of the user and emit light toward the inside the finger skin, and may measure a biometric signal by using the light reflected from the inside of the skin. Biometric signals measured by the smart ring may be transmitted to the outside, and based on the biometric signals, values related to cardiovascular exercise such as the user's blood pressure, heart rate, and heart rate variability may be measured.

The smart ring may communicate with an external electronic device and transmit biometric signals measured by the electronic device. The smart ring may also be controlled through an electronic device. For example, the electronic device may be any type of handheld wireless communication device such as a smart phone, tablet PC, or laptop. Smart rings and electronic devices may communicate with each other through, for example, 3G, 4G, 5G, 3GPP (3rd Generation Partnership Project), LTE (Long Term Evolution), WIMAX (World Interoperability for Microwave Access), Wi-Fi, Bluetooth communication, infrared communication, ultrasonic waves, Visible Light Communication (VLC), LiFi, etc.

Hereinafter, embodiments of the present disclosure will be described in detail with reference to the attached drawings.

FIG. 1 is a block diagram of a smart ring according to an example embodiment of the present disclosure.

Referring to FIG. 1, a smart ring 100 may include at least one light-emitting circuit 110, a plurality of driving circuits 121, 122, and 123, a switch 130, and a sensing circuit 140. Hereinafter, for convenience of description, the at least one light-emitting circuit 110, the plurality of driving circuits 121, 122, and 123, the switch 130, and the sensing circuit 140 are referred to as biometric sensors.

The smart ring 100 may include at least one light-emitting circuit 110. Each light-emitting circuit 110 may include first to third light sources 111, 112, and 113. The first to third light sources 111, 112, and 113 may each include a light-emitting diode (LED) that generates light of first to third wavelengths. The first to third wavelengths may include, but are not limited to, a red region, a green region, and an infrared region, respectively.

Light generated from the first to third light sources 111, 112, and 113 may enter the inside of the skin that is in contact with the smart ring 100. Within a skin tissue, some light is absorbed and/or scattered, and some light is transmitted and/or reflected. The transmitted and/or reflected light may be sensed by the sensing circuit 140.

The switch 130 may control each light-emitting circuit 110. The switch 130 may include, but is not limited to, a MOS transistor. As the switch 130 controls the light-emitting circuit, the plurality of light sources 111, 112, and 113 included in the light-emitting circuit may be controlled.

The sensing circuit 140 may sense reflected light that is generated in the first to third light sources 111, 112, and 113 and reflected from at least one of blood vessels and tissues within the skin. The sensing circuit 140 may include at least one diode. The sensing circuit 140 may sense all reflected light generated in the first to third light sources 111, 112, and 113. That is, the wavelength range of reflected light sensed by the sensing circuit 140 is not limited. Referring to FIG.

1, at least one light-emitting circuit 110 may share the sensing circuit 140. However, the sensing circuit 140 may also be provided in each light-emitting circuit 110.

The first to third driving circuits 121, 122, and 123 may control the first to third light sources 111, 112, and 113, respectively. For example, the first to third driving circuits 121, 122, and 123 may sequentially turn on the first to third light sources 111, 112, and 113. Respectively. The first to third driving circuits 121, 122, and 123 may control the first to third light sources 111, 112, and 113 based on biometric signals measured by the smart ring 100, a control signal generated by an external electronic device, and temperature of the skin that is in contact with the smart ring 100.

In addition, the first to third driving circuits 121, 122, and 123 may control the first to third light sources 111, 112, and 113 according to the positions of light-emitting circuits including the first to third light sources 111, 112, and 113.

Although not shown, the smart ring 100 may further include a control unit that controls the switch 130, the sensing circuit 140, and the first to third driving circuits 121, 122, and 123, and further include a temperature sensor that measures the temperature of the skin in contact with the smart ring 100. Additionally, the smart ring 100 may further include a communication unit that transmits measured biometric signals and temperature to an electronic device and receives a control signal.

Figure 2:
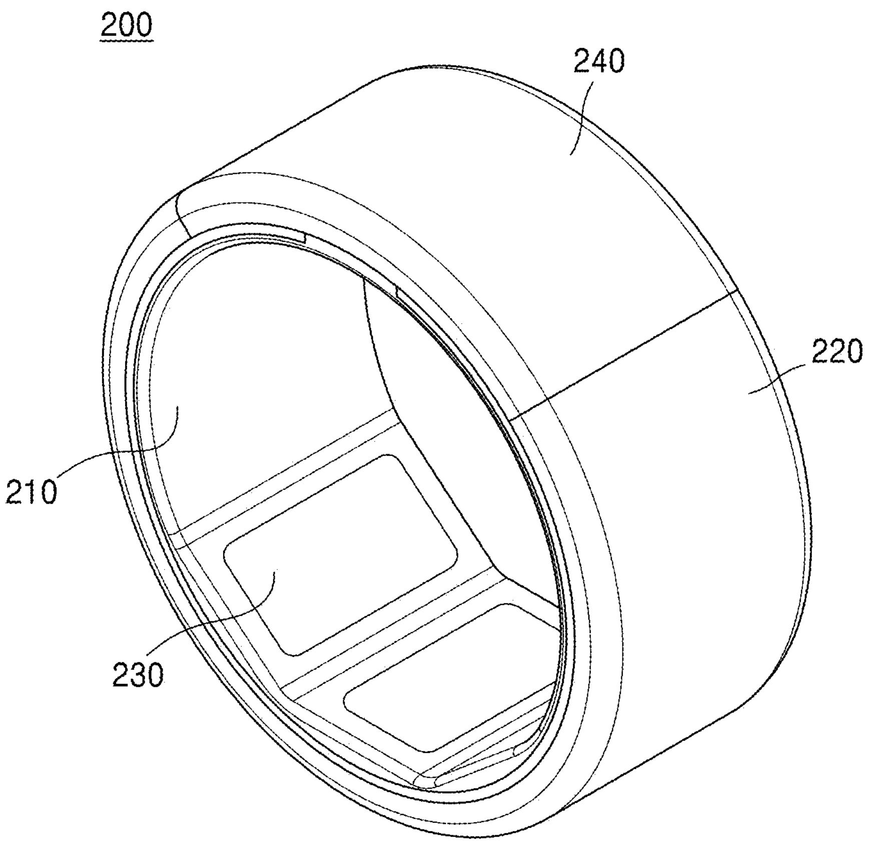
FIG. 2 is an example diagram illustrating a shape of a smart ring according to an example embodiment of the present disclosure.

FIG. 2 is an exemplary diagram illustrating the shape of a smart ring according to an example embodiment of the present disclosure.

Referring to FIG. 2, a smart ring 200 may include first and second electrodes 210 and 220, an insulating unit 230, and a top cover 240, and may further include a control unit, a printed circuit board, and a battery thereinside.

The first electrode 210 may be provided in a ring shape, may include a conductor, and may be inserted into the user's finger and come into contact with the finger. The second electrode 220 may be assembled on the outside of the first electrode 210, may include a conductor, and may be in contact with the user's body. A surface on which the first electrode 210 is provided is referred to as an inner side surface of the smart ring 200.

The smart ring 200 may include a plurality of insulating units 230. The insulating unit 230 may be disposed between the first electrode 210 and the second electrode 220 to maintain insulation between the first electrode 210 and the second electrode 220. Additionally, the insulating unit 230 may include the biometric sensor of FIG. 1. Biometric sensors may measure biometric signals such as electrocardiogram (ECG) and photoplethysmography (PGG).

For example, the biometric sensor may have a flat plate shape or a protruding shape. When a biometric sensor is formed in a plate shape, the biometric sensor may provide an excellent fit to the user, and when formed in a protruding shape, the degree of adhesion of the biometric sensor to the user's finger increases, thereby increasing the accuracy of biometric signal sensing. In FIG. 2, a portion where the biometric sensor is provided is illustrated in a flat plate shape, but is not limited thereto and may be configured with a curved surface like the outside of the smart ring 200.

The control unit may be disposed between the first electrode 210 and the second electrode 220, and may collect biometric signals when the second electrode 220 contacts the body of the user except the fingers.

The second electrode 220 may be configured in an arc shape, and the top cover 240 may be provided on one side of the second electrode 220. The second electrode 220 may be assembled by approaching from the side of the first electrode 210 or the insulating unit 230, and the top cover 240 may be assembled on the opposite side. Additionally, inside the second electrode 220, a printed circuit board and a battery may be included. A surface on which the second electrode 220 is provided is referred to as an outer side surface of the smart ring 200.

The printed circuit board may include a flexible material that is easily bendable, and the control unit and the components of FIG. 1 may be mounted on the printed circuit board. The printed circuit board may include a communication module for communication with an external electronic device. The battery may provide power so that current flows through the first and second electrodes 210 and 220, and provide power to the printed circuit board, including the control unit.

Figure 3:
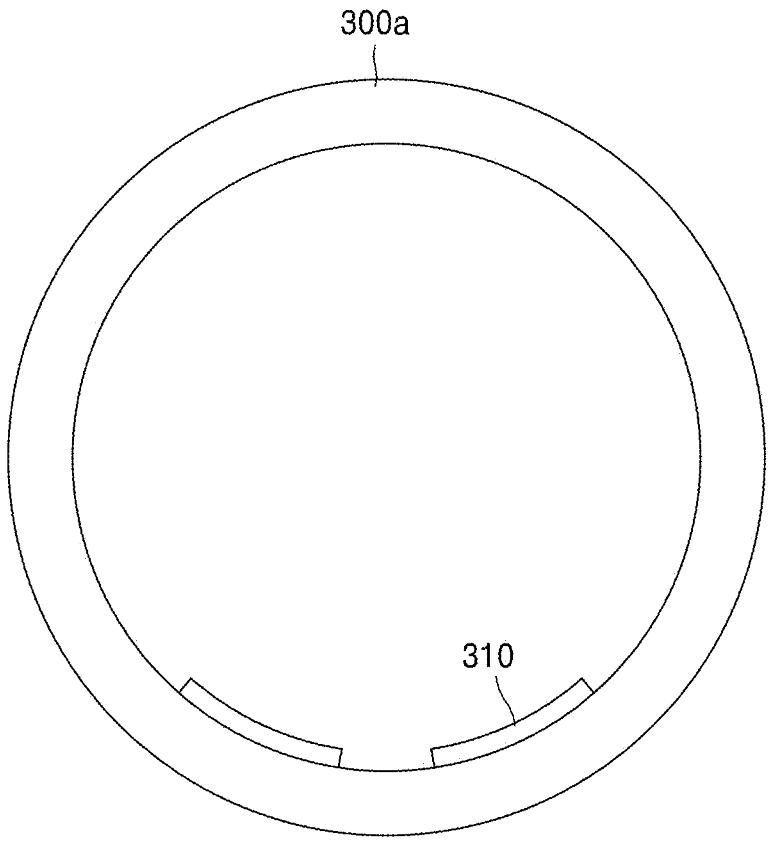
FIGS. 3 and 4 are example diagrams illustrating a cross-section of a smart ring according to an example embodiment of the present disclosure.
Figure 4:
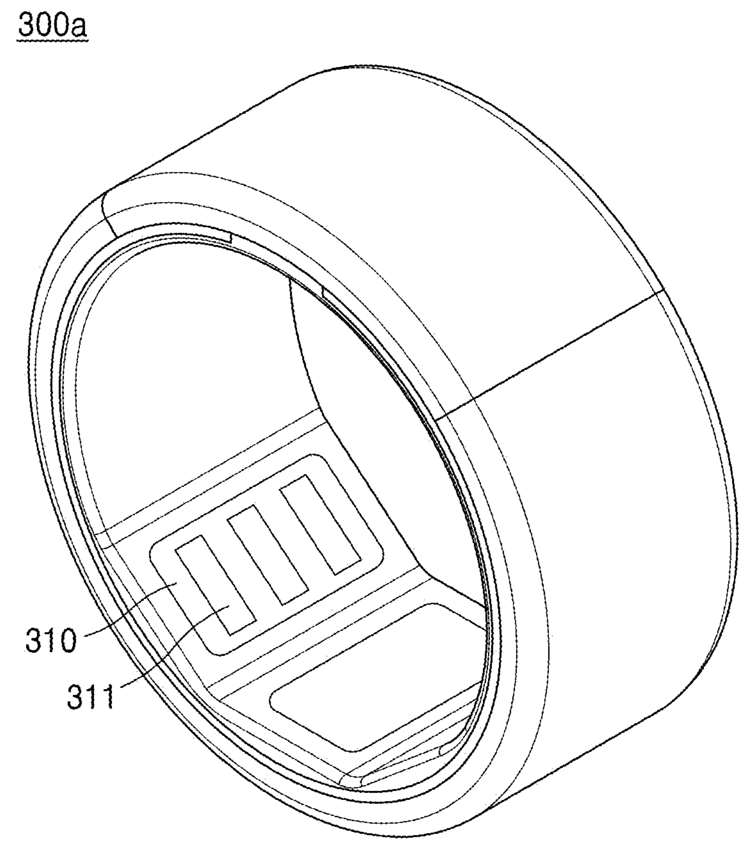

FIGS. 3 and 4 are exemplary diagrams illustrating a cross-section of a smart ring according to an example embodiment of the present disclosure.

In the present specification, an inner side surface of a smart ring 300*a*, which is in contact with the user's finger, is referred to as a first surface, and an outer side surface of the smart ring 300*a* is referred to as a second surface. Referring to FIG. 3, a biometric sensor may be provided on the first surface of the smart ring 300*a*. For example, a biometric sensor including two light-emitting circuits 310 may be provided, and each light-emitting circuit 310 may be adjacent to each other.

Referring to FIG. 4, each light-emitting circuit 310 may include a first light source 311, a second light source, and a third light source.

The first light source 311 of the first light-emitting circuit 310 and a first light source of a second light-emitting circuit may be arranged to be adjacent to each other. That is, light sources that generate light of a same wavelength may be arranged adjacent to each other. The order in which the first to third light sources are arranged within each light-emitting circuit may be determined depending on the wavelength of the first to third light sources.

As an example, the first light source 311 of the first light-emitting circuit 310 and the first light source of the second light-emitting circuit may operate as one group. For example, the first driving circuit 121 that drives the first light source 311 may simultaneously drive the first light source 311 of the first light-emitting circuit 310 and the first light source of the second light-emitting circuit. As an example, the first driving circuit may sequentially drive the first light source 311 of the first light-emitting circuit 310 and the first light source of the second light-emitting circuit.

As an example, the first to third light sources may be sequentially arranged in a first direction corresponding to the height direction of the smart ring.

The biometric sensor may be arranged similarly to the shape illustrated in FIG. 1. That is, a plurality of light sources may be arranged in a matrix, and driving circuits and a switch that control each light source may be arranged at the edge of the matrix. Accordingly, the number of light sources mounted on a smart ring which has a relatively small area may be increased, and as the intensity of light increases, the accuracy of measured biometric signals may also be increased. In FIGS. 3 and 4, the biometric sensor includes two light-emitting circuits 310, but is not limited thereto.

Figure 5:
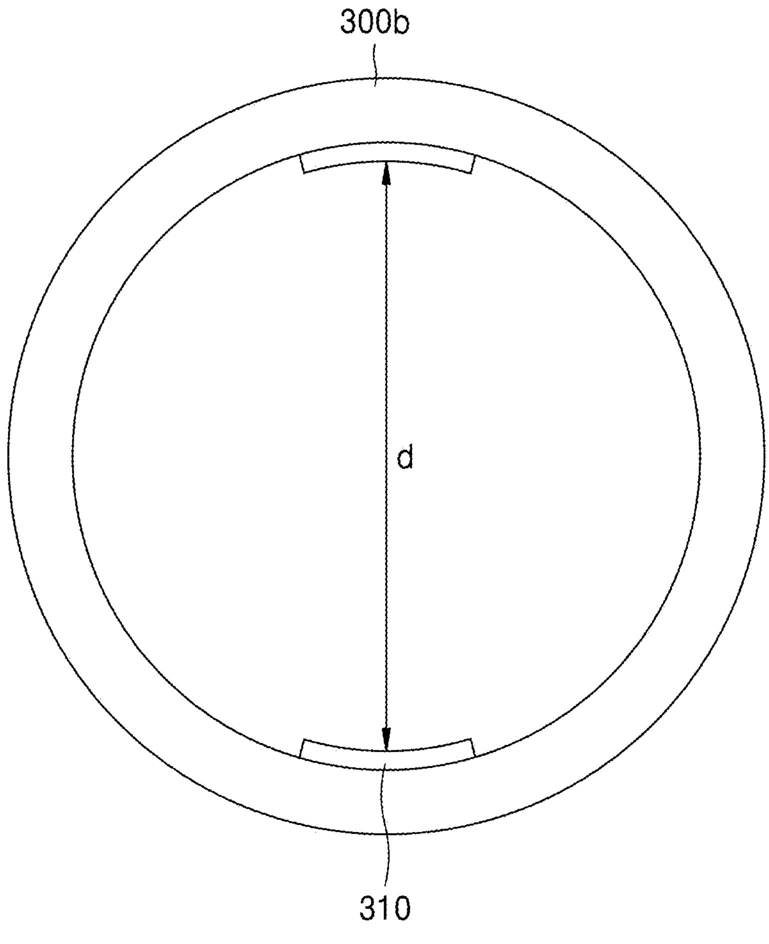
FIG. 5 is an example diagram illustrating a cross-section of a smart ring according to an example embodiment of the present disclosure.

FIG. 5 is an exemplary diagram illustrating a cross-section of a smart ring according to an example embodiment of the present disclosure.

Referring to FIG. 5, like FIGS. 3 and 4, the biometric sensor includes two light-emitting circuits 310, and in this case, each light-emitting circuit 310 may be arranged apart from each other. For example, a distance between each light-emitting circuit 310 may be a diameter (d) of the smart ring (300*b*). The light-emitting circuit 310 adjacent to a sensing circuit may sense light reflected from the user's finger, and the light-emitting circuit 310 away from the sensing circuit may sense light transmitted through the user's finger. Accordingly, the smart ring 300*b* may increase the signal accuracy by measuring biometric signals in various forms.

Here, a driver and a switch may drive a light-emitting circuit adjacent to the sensing circuit and a light-emitting circuit distant from the sensing circuit differently. For example, first to third light sources of the light-emitting circuit adjacent to the sensing circuit may be sequentially driven, and then the first to third light sources of the light-emitting circuit distant from the sensing circuit may be sequentially driven, but this is merely a description of an example.

Figure 6:
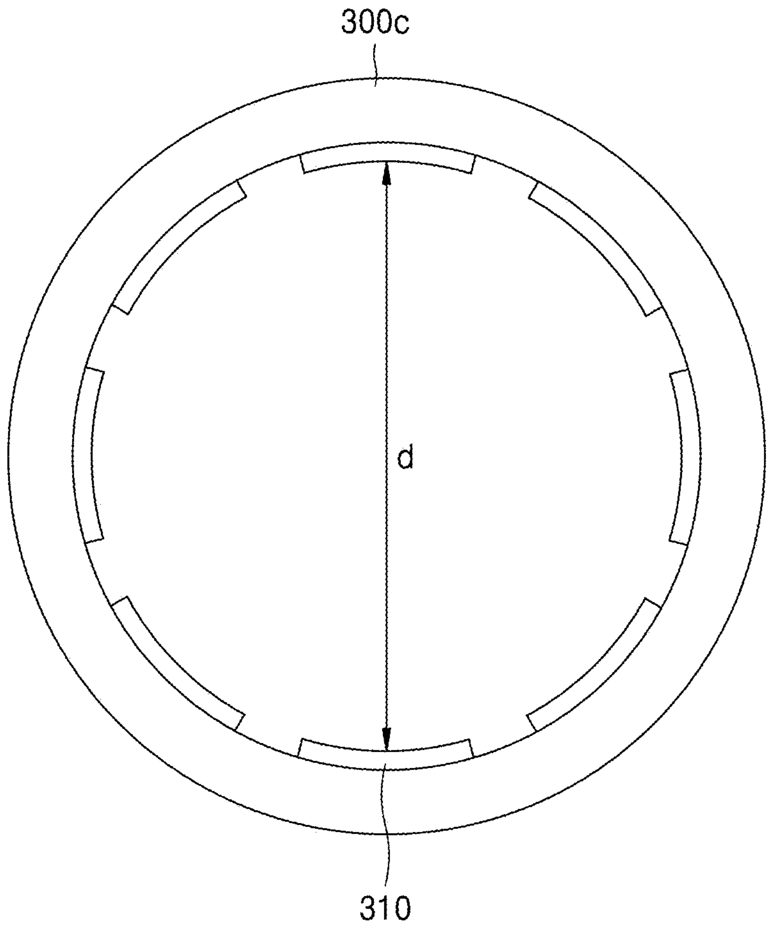
FIG. 6 is an example diagram illustrating a cross-section of a smart ring according to an example embodiment of the present disclosure.

FIG. 6 is an exemplary diagram illustrating a cross-section of a smart ring according to an example embodiment of the present disclosure.

Referring to FIG. 6, a smart ring 300*c* may include a plurality of light-emitting circuits 310. Each light-emitting circuit 310 may be uniformly disposed on the first surface. That is, each light-emitting circuit 310 may be arranged apart from each other at an equal distance. Accordingly, as a uniform degree of pressure is applied to the finger inserted into the smart ring 300*c*, the user's wearing comfort may be improved. Additionally, since the light-emitting circuit 310 has a shape surrounding a finger, the accuracy of a measured signal may be increased.

A light-emitting circuit disposed on the bottom surface of the finger and a light-emitting circuit disposed on the top surface of the finger may each output light of different intensities. For example, a light-emitting circuit in contact with the skin close to the blood vessel may output light of low intensity, and a light-emitting circuit in contact with the skin far from the blood vessel may output light with a strong intensity. As the output of the light-emitting circuit is determined, a direction in which the smart ring is worn may be determined. Accordingly, the smart ring 300*c* may further include an alarm unit, and the alarm unit may generate an alarm when the smart ring 300*c* is not worn in a set direction.

Figure 7:
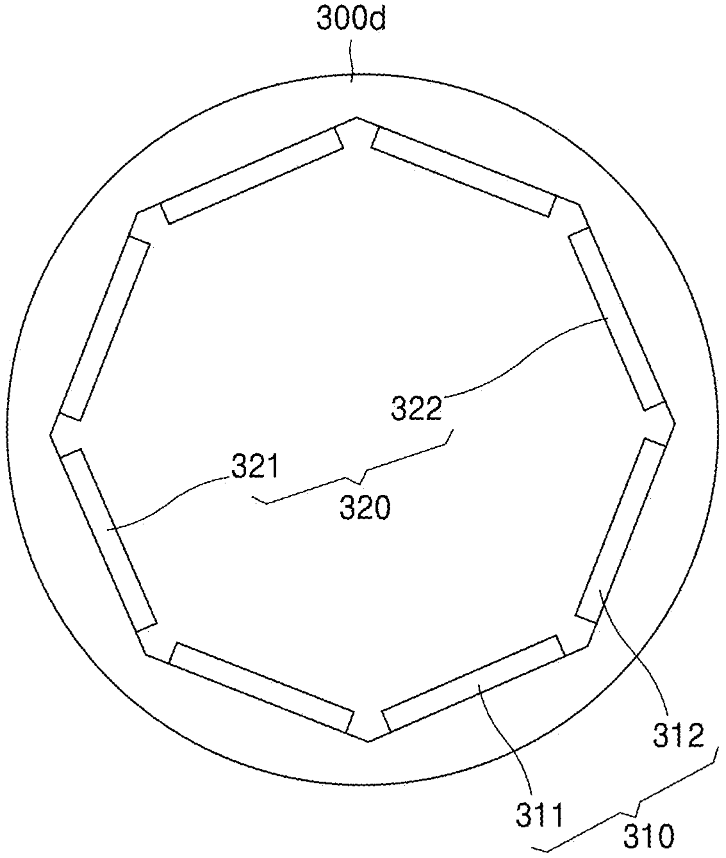
FIG. 7 is an example diagram illustrating a cross-section of a smart ring according to an example embodiment of the present disclosure.

FIG. 7 is an exemplary diagram illustrating a cross-section of a smart ring according to an example embodiment of the present disclosure.

Referring to FIG. 7, an inner side surface of a smart ring 300*d* may have a polygonal pillar shape. Accordingly, each light-emitting circuit 311, 312, 321, and 322 of a biometric sensor may be provided on each side of the polygonal pillar. Each light-emitting circuit 311, 312, 321, and 322 may include first to third light sources, and the first to third light sources may be arranged as described with reference to FIG. 4. In FIG. 7, a light-emitting circuit is illustrated on all sides of the polygonal pillar, but also, a light-emitting circuit may be provided on at least one side thereof.

The plurality of light-emitting circuits 311, 312, 321, and 322 may be divided into a first group 310 and a second group 320. The light-emitting circuits 311 and 312 of the first group 310 may be driven in a first operation mode, and the light-emitting circuits 321 and 322 of the second group 320 may be driven in a second operation mode. That is, when the smart ring 300*d* is set to the second operation mode, a switch may turn off the light-emitting circuits 311 and 312 belonging to the first group 310 and turn on the light-emitting circuits 321, 322 belonging to the second group 320.

The first and second operating modes may be set by an electronic device that communicates with the smart ring 300*d*. For example, the first operation mode may correspond to a reflective biometric sensor, and the second operation mode may correspond to a transmissive biometric sensor.

For example, the first and second light-emitting circuits 311 and 312 may belong to the first group 310, and the third and fourth light-emitting circuits 321 and 322 may belong to the second group 320. The first and second light-emitting circuits 311 and 312 may be disposed on adjacent sides of the polygonal pillar, and the third and fourth light-emitting circuits 321 and 322 may be disposed on opposite sides of the polygonal pillar, which face each other.

First to third driving circuits that respectively control the first to third light sources of each light-emitting circuit may control cycles for controlling the first to third light sources such that a cycle for driving the first to third light sources of each of the first and second light-emitting circuits 311 and 312 is different from a cycle for driving the first to third light sources of each of the third and fourth light-emitting circuits 321 and 322.

That is, the first to third driving circuits may control the cycle for driving the light sources according to an operation mode. For example, in the first operation mode, the first to third light sources may be sequentially driven in a first cycle, and in the second operation mode, the first to third light sources may be sequentially driven in a second cycle. Additionally, the first to third driving circuits may control the order of driving the light sources according to the operation mode.

Figure 8:
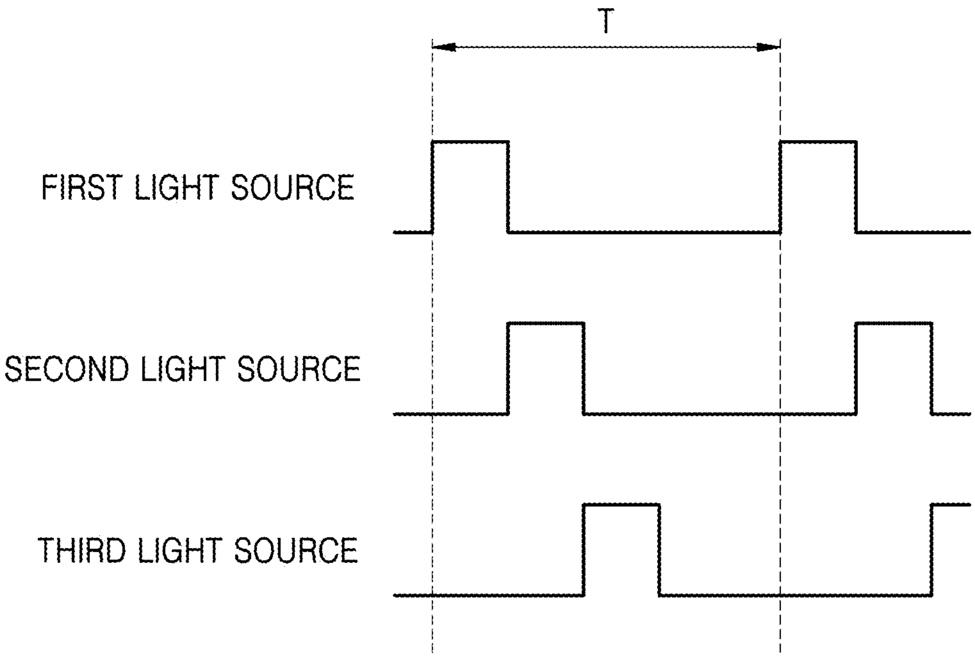
FIG. 8 is a timing diagram illustrating wavelengths generated from a plurality of light sources according to an example embodiment of the present disclosure.

FIG. 8 is a timing diagram illustrating wavelengths generated from a plurality of light sources according to an example embodiment of the present disclosure.

Referring to FIG. 8, the first to third light sources may be driven sequentially and periodically. For example, during a first cycle T, the first to third light sources may be driven sequentially. The cycle may vary depending on a location where the first to third light sources are provided in a smart ring, and the order in which each light source is driven may also vary.

For example, a cycle in which the first to third light sources are driven based on at least one of a biometric signal measured by a smart ring, a control signal generated based on the biometric signal, and temperature of the skin of the user measured by the smart ring may vary.

As above, example embodiments have been disclosed in the drawings and specification. In the present specification, embodiments have been described using specific terms, but these are only used for the purpose of explaining the technical idea of the present disclosure and not used to limit the meaning or scope of the present disclosure described in the claims. Therefore, it will be understood by those skilled in the art that various modifications and other equivalent embodiments are possible therefrom. Therefore, the true technical protection scope of the present disclosure should be determined by the technical spirit of the attached claims.

The invention claimed is:

1. A smart ring for sensing a biometric signal by coming in contact with the skin, the smart ring comprising:

at least one light-emitting circuit including first to third light sources that respectively generate light of first to third wavelengths incident on the inside of the skin at non-overlapping first to third points in time;

a switch that controls each of the at least one light-emitting circuit;

first to third driving circuits that respectively control the first to third light sources of each light-emitting circuit; and a sensing circuit configured to obtain reflected light that is output from the at least one light-emitting circuit and reflected from the inside of the skin;

wherein an inner side surface of the smart ring, which is in contact with the skin, is formed as a polygonal pillar, each light-emitting circuit is provided on each side of the polygonal pillar, and a first light-emitting circuit group of the at least one light-emitting circuit operates in a first operation mode, and a second light-emitting circuit group of the at least one light-emitting circuit operates in a second operation mode.

2. The smart ring of claim 1, wherein the at least one light-emitting circuit comprises first and second light-emitting circuits provided on an inner side surface where the smart ring and the skin contact each other, and the first and second light-emitting circuits are arranged adjacent to each other.

3. The smart ring of claim 2, wherein a light source that generates light of the first wavelength in the first light-emitting circuit and a light source that generates light of the first wavelength in the second light-emitting circuit are arranged adjacent to each other.

4. The smart ring of claim 1, wherein the at least one light-emitting circuit includes first and second light-emitting circuits provided on an inner side surface where the smart ring and the skin contact each other, and the first and second light-emitting circuits are arranged such that a distance between the first and second light-emitting circuits is equal to a diameter of the smart ring.

5. The smart ring of claim 1, wherein the at least one light-emitting circuit comprises first to nth light-emitting circuits (where n is a natural number equal to or greater than 3) provided on an inner side surface where the smart ring and the skin contact each other, and the first to nth light-emitting circuits are uniformly disposed on the inner side surface.

6. The smart ring of claim 1, wherein the first light-emitting circuit group comprises first and second light-emitting circuits respectively disposed on adjacent sides of the polygonal pillar, and the second light-emitting circuit group comprises third and fourth light-emitting circuits respectively disposed on opposite sides of the polygonal pillar which face each other.

7. The smart ring of claim 6, wherein first to third light sources of the first to fourth light-emitting circuits are sequentially arranged in a first direction corresponding to a height direction of the smart ring.

8. The smart ring of claim 1, wherein the first to third driving circuits sequentially drive first to third light sources of each of the first and second light-emitting circuits in the first operation mode, and sequentially drive first to third light sources of each of the third and fourth light-emitting circuits in the second operation mode.

9. The smart ring of claim 8, wherein the first to third wavelengths comprise a red region, a green region, and an infrared region, respectively.

10. The smart ring of claim 8, wherein the first to third driving circuits control each cycle of driving each of the first to third light sources of each light-emitting circuit according to at least one of the biometric signal and a control signal generated based on the biometric signal.

11. The smart ring of claim 10, wherein the first to third driving circuits control cycles for driving the first to third light sources such that a driving cycle of the first to third light sources of each of the first and second light-emitting circuits is different from a driving cycle of the first to third light sources of each of the third and fourth light-emitting circuits.

12. The smart ring of claim 10, further comprising a temperature sensor that measures a temperature of the skin, wherein the first to third driving circuits control each cycle for driving each of the first to third light sources of each light-emitting circuit based on the temperature measured by the temperature sensor.

* * * * *